(12) United States Patent
Nishimura et al.

(10) Patent No.: US 10,894,122 B2
(45) Date of Patent: Jan. 19, 2021

(54) APPLICATION MEMBER AND MEDICAL INSTRUMENT

(71) Applicant: TERUMO KABUSHIKI KAISHA, Tokyo (JP)

(72) Inventors: Kanako Nishimura, Nakano-ku (JP); Shuhei Sasazawa, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 221 days.

(21) Appl. No.: 16/002,360

(22) Filed: Jun. 7, 2018

(65) Prior Publication Data

US 2018/0280609 A1 Oct. 4, 2018

Related U.S. Application Data

(63) Continuation of application No. PCT/JP2016/003785, filed on Aug. 18, 2016.

(30) Foreign Application Priority Data

Jan. 14, 2016 (JP) ................. 2016-005410

(51) Int. Cl.
*A61M 5/142* (2006.01)
*A61F 13/02* (2006.01)
*A61M 5/172* (2006.01)

(52) U.S. Cl.
CPC ......... *A61M 5/14248* (2013.01); *A61F 13/02* (2013.01); *A61M 5/1723* (2013.01); *A61M 2209/088* (2013.01); *A61M 2230/201* (2013.01)

(58) Field of Classification Search
CPC ............ A61M 5/14248; A61M 5/1723; A61M 2209/088; A61M 2230/201;
(Continued)

(56) References Cited

U.S. PATENT DOCUMENTS

| 5,599,289 A | 2/1997 | Castellana |
| 5,807,341 A | 9/1998 | Heim |

(Continued)

FOREIGN PATENT DOCUMENTS

| CN | 1553821 A | 12/2004 |
| CN | 1968638 A | 5/2007 |

(Continued)

OTHER PUBLICATIONS

International Search Report with English language translation and Written Opinion issued in International Application No. PCT/JP2016/003785 dated Nov. 15, 2016.

(Continued)

*Primary Examiner* — Theodore J Stigell
*Assistant Examiner* — Daniel Moore
(74) *Attorney, Agent, or Firm* — Foley & Lardner LLP

(57) ABSTRACT

A sheet-shaped application member includes: a first region, and a second region extending around the first region, wherein: the first region comprises a first region attachment surface to which a medical device is attachable, and a first region application surface opposite the first region attachment surface and adapted to be applied to a subject, the second region comprises a second region application surface adapted to be applied to the subject, and the first and second application regions are adapted such that, when the application member is applied to the subject, adhesion at the second region application surface is stronger than adhesion at the first region application surface; and an application member tear portion adapted to allow for tearing of a portion within the first region or for tearing the first region from the second region.

11 Claims, 12 Drawing Sheets

(58) Field of Classification Search
CPC .......... A61M 2025/0266; A61M 25/02; A61M 2025/02; A61M 2025/0253; A61F 13/02; A61B 5/14532; A61B 46/00
See application file for complete search history.

(56) References Cited

U.S. PATENT DOCUMENTS

| | | | |
|---|---|---|---|
| 2003/0195599 A1* | 10/2003 | Bishay | ............... A61N 1/36021 607/116 |
| 2004/0116866 A1 | 6/2004 | Gorman et al. | |
| 2008/0077081 A1* | 3/2008 | Mounce | .............. A61M 5/1413 604/67 |

FOREIGN PATENT DOCUMENTS

| | | | |
|---|---|---|---|
| CN | 101855094 | A | 10/2010 |
| CN | 202801937 | U | 3/2013 |
| EP | 0 638 301 | A1 | 2/1995 |
| JP | H07-67911 | A | 3/1995 |
| JP | 2001-506523 | A | 5/2001 |
| JP | 2002-522178 | A | 7/2002 |
| JP | 2004-538107 | A | 12/2004 |
| JP | 2006-006489 | A | 1/2006 |
| JP | 5102350 | B2 | 12/2012 |
| WO | WO-98/25661 | A1 | 6/1998 |
| WO | WO-00/09202 | A1 | 2/2000 |
| WO | WO-03/015867 | A2 | 2/2003 |

OTHER PUBLICATIONS

Office Action dated Apr. 28, 2020 in corresponding Chinese Patent Application No. 201680061254.

* cited by examiner

APPLICATION MEMBER AND MEDICAL INSTRUMENT

CROSS-REFERENCE TO RELATED APPLICATIONS

The present application is a Bypass Continuation of PCT Application No. PCT/JP2016/003785, filed on Aug. 18, 2016, which claims priority to Japanese Application No. 2016-005410, filed on Jan. 14, 2016. The contents of these applications are hereby incorporated by reference in their entireties.

BACKGROUND

Technical Field

The present disclosure relates to an application member and a medical instrument.

Background Art

It is known to apply a medical instrument to a subject's skin when the subject uses the medical instrument continuously over a period of about several days to several weeks. For example, JP 5102350 B2 discloses using a delivery device for delivering a fluid, such as a medical fluid, by applying the delivery device to a subject's body.

SUMMARY

In order to inhibit the medical instrument from peeling off and falling off the subject's skin when the medical instrument is applied to the subject for days to weeks, it is preferable to apply the medical instrument to the subject using a patch having strong adhesion. On the other hand, applying the medical instrument to the subject with a patch having strong adhesion tends to irritate the skin when removing the medical instrument from the skin such as to end the use of the medical instrument. That is, the stronger the adhesion capability of the patch, the more difficult it is to remove the medical instrument from the skin, and this may cause reddening or peeling of the skin when removing the medical instrument from the skin. The subject will also tend to feel pain when removing the medical instrument from the skin.

In view of the foregoing problems, it is an object of the present invention to provide an application member that can ensure adhesive strength between a medical instrument and the skin and that can reduce pain when removing the medical instrument from the skin, and a medical instrument that includes such an application member.

As one aspect of the present invention, an application member is a sheet-like application member having an application surface to be applied and adhered to a subject, and includes a first region having an attachment surface to which a medical device can be attached, the attachment surface being different from the application surface, a second region having stronger adhesion in the application surface than the first region and provided around the first region, and a tear portion capable of tearing a portion within the first region or of tearing apart the first region and the second region.

As one embodiment of the present invention, the first region preferably has a slit or a tear portion provided from the tear portion toward the center of the first region.

As one embodiment of the present invention, the second region preferably has a slit or a tear portion provided from an outer peripheral edge of the second region toward the tear portion.

As one embodiment of the present invention, the outer peripheral edge of the second region is preferably substantially polygonal, and the second region preferably has a protrusion protruding in a direction opposite the first region on at least any one side.

As one embodiment of the present invention, the first region is preferably substantially polygonal and preferably has a protrusion protruding toward the second region on at least any one side.

As one embodiment of the present invention, the second region is preferably oval.

As one embodiment of the present invention, the application member preferably includes two of the slits or two other tear portions connecting the outer peripheral edge of the second region with the tear portion.

As one embodiment of the present invention, the two slits or the two other tear portions preferably extend linearly substantially in parallel.

As one embodiment of the present invention, the application member is preferably oval and the two slits or the two tear portions preferably extend linearly substantially in parallel along a longitudinal axis of the oval.

As one embodiment of the present invention, the application member preferably further includes a third region in a portion of the first region, the third region having stronger adhesion in the application surface than a surrounding area.

As one aspect of the present invention, an application member includes a sheet-like first member having an application surface to be applied to a subject, and a second member having an application surface to be applied to the subject, the application surface of the second member having stronger adhesion than the application surface of the first member, and the first member and the second member being laid on top of each other, wherein the first member has a tear portion capable of annularly tearing the first member, the second member is annular having an outer peripheral edge and an inner peripheral edge, and the inner peripheral edge of the second member is positioned outside the tear portion of the first member, an outer peripheral edge of the first member is positioned outside the inner peripheral edge of the second member, and the outer peripheral edge of the second member is positioned outside the outer peripheral edge of the first member.

As one aspect of the present invention, a medical instrument includes a medical device, and a sheet-like application member having an attachment surface to which the medical device is attached and an application surface to be attached to a subject, wherein the application member includes a first region to which the medical device is attached, a second region having stronger adhesion in the application surface than the first region and provided around the first region, and a tear portion capable of tearing a portion within the first region or of tearing apart the first region and the second region.

According to certain embodiments described herein, an application member that can provide good adhesive strength between a medical instrument and the skin and that can reduce pain when removing the medical instrument from the skin, and a medical instrument that includes such an application member, can be provided.

DETAILED DESCRIPTION

Figure 1:
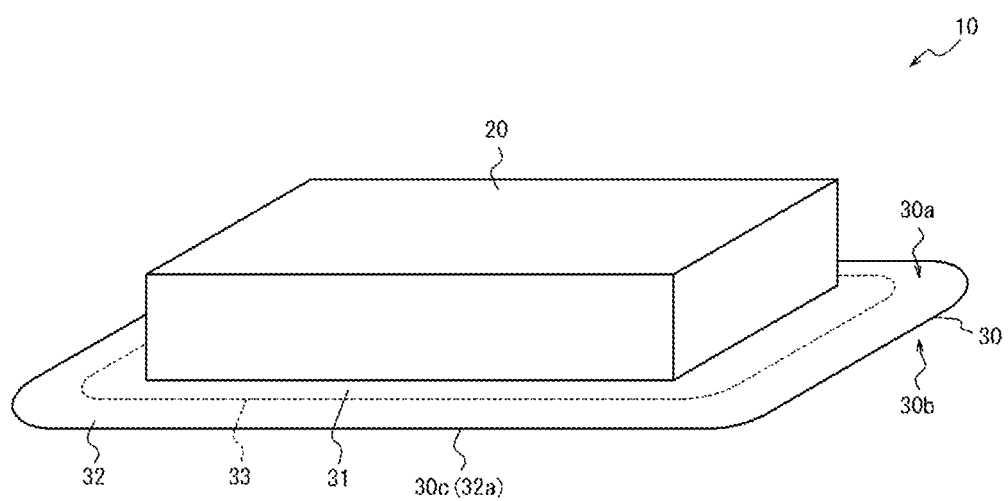
FIG. 1 is a schematic perspective view of a medical instrument according to an embodiment of the present invention.

A medical instrument according to embodiments of the present invention will now be described with reference to the drawings. Like parts in the drawings have been given the same reference numerals.

FIG. 1 is a schematic perspective view of a medical instrument according to an embodiment of the present invention. As shown in FIG. 1, a medical instrument 10 includes a medical device 20 and an application member 30 to which the medical device 20 is attached. The medical instrument 10 is to be used by a subject continuously, for example, for a period of about several days to several weeks. The subject uses the medical instrument 10 by applying the application member 30 of the medical instrument 10 to the subject's skin.

The medical device 20 may be one of a variety of medical devices depending, for example, on the purpose of use or application of the medical instrument 10. The medical device 20 is, for example, a measurement device that has a control unit that continuously measures biological information of a subject. An example of such a measurement device is a device that calculates glucose values in the subcutaneous tissue by Continuous Glucose Monitoring (CGM). In this case, the subject, for example, connects the measurement device to a sensor inserted into the body using a puncturing tool and applies the measurement device to the skin to carry out CGM. The medical device 20 may also be, for example, a medical fluid pump that injects a fluid, such as a medical fluid, into the body. An example of such a medical fluid pump is an insulin pump. It should be noted that the medical device 20 may be a device other than those mentioned above.

The application member 30 is a sheet-like member and has an attachment surface 30a to which the medical device 20 is attached and an application surface 30b that is applied to the subject's skin. The application member 30 may be made, for example, of a rayon nonwoven fabric, a polyester nonwoven fabric, a polyurethane nonwoven fabric, or a plastic (polyethylene, polyester, polyurethane, etc.) core material. Hereinafter, the attachment surface 30a side of the application member 30 of the medical instrument 10 may also be referred to as an "upper side" and the application surface 30b side thereof may be referred to as a "lower side."

Figure 2:
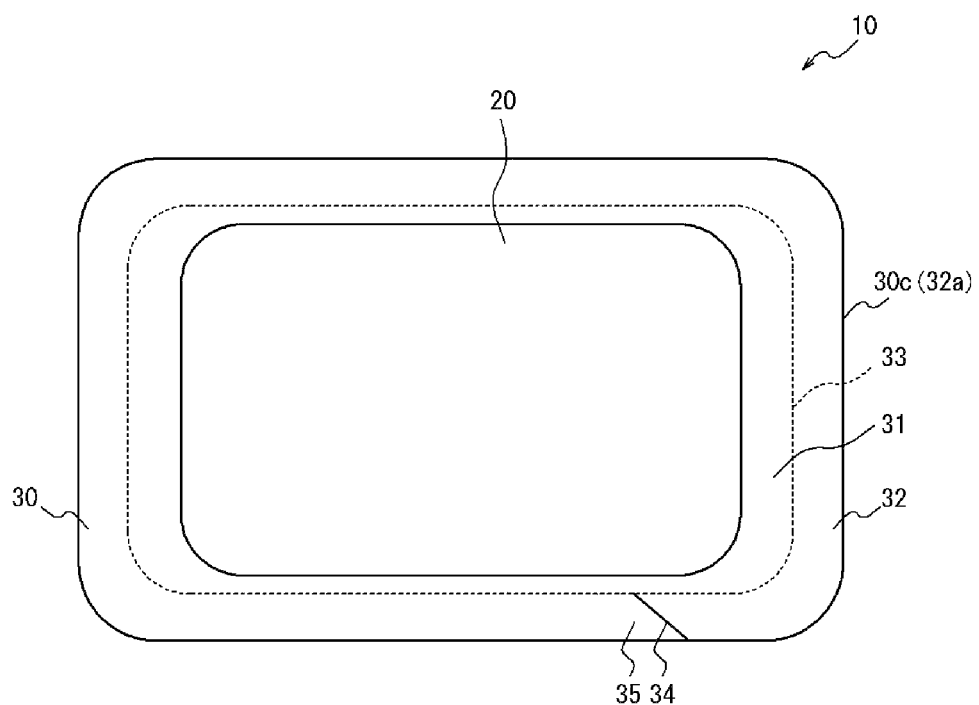
FIG. 2 is a schematic top view of an example of the medical instrument shown in FIG. 1.

The application member 30 has a first region 31 and a second region 32. The second region 32 is provided around the first region 31. That is, the application member 30 has the first region 31 provided at a center region and the second region 32 provided at a region of an outer peripheral edge 30c when viewed from the top, such as shown in FIG. 2. A tear portion 33 (i.e., an "application member tear portion") is provided between the first region 31 and the second region 32. The tear portion 33 is formed as a linear portion that is capable of being torn to separate the first region 31 from the second region 32. The tear portion 33 may be, for example, a perforation provided on the application member 30. A subject may tear the tear portion 33 to separate the first region 31 from the second region 32 when removing the applied medical instrument 10 from the skin.

The medical device 20 is attached to the attachment surface 30a of the first region 31 of the application member 30. The medical device 20 can be attached to the application member 30 in any manner and can be attached, for example, by adhesion or welding. Glue is used in the case of adhesion. A thermal weld, an ultrasonic weld, a high-frequency weld, a laser weld, or the like is used in the case of welding. The area of the attachment surface 30a of the first region 31 is larger than the area of a portion (i.e., a bottom side) of the medical device 20 that is to be attached to the attachment surface 30a.

An adhesive that is capable of applying the application member 30 to the subject's skin is applied to the application surface 30b of the application member 30. The adhesive is applied to the application surface 30b such that the adhesion of the second region 32 is stronger than the adhesion of the first region 31 in the application surface 30b.

Specifically, the adhesion of the application surface 30b of the second region 32 to the skin is preferably strong enough so that the medical instrument 10 does not peel off the subject's skin for the period (for example, of about several days to several weeks) during which the subject uses the medical instrument 10 and is stronger than the adhesion of usual wound bandages, and the like. In particular, because an outer peripheral edge 32a of the second region 32 is more likely to peel off than other parts of the application member 30, the adhesion of the outer peripheral edge 32a of the second region 32 is preferably strong enough so that the medical instrument 10 does not peel off the subject's skin while the subject is using the medical instrument 10. On the other hand, the adhesion of the application surface 30b of the first region 31 to the skin is preferably strong enough to maintain a certain adhesiveness to the skin over the period during which the subject uses the medical instrument 10 while preventing the subject from feeling too much pain when removing the medical instrument 10 from the skin.

The difference in adhesion (adhesive strength or adhesive capability) between the first region 31 and the second region 32 can be made, for example, by applying adhesives of different types (having different components) to the application surface 30b of each of the first region 31 and the second region 32. The difference in adhesion can also be made, for example, by changing the amount of adhesive applied to the application surface 30b of each of the first region 31 and the second region 32. The difference in adhesion can also be made, for example, by a difference in the areas to which the adhesive is applied in the application surface 30b of each of the first region 31 and the second region 32. Silicone adhesives, acrylic adhesives, rubber (such as natural rubber or synthetic rubber) adhesives, or others can be used as the adhesive. However, the adhesive is not limited to the adhesives listed herein.

Detailed construction of the application member 30 will now be described with reference to FIGS. 2 to 15.

FIG. 2 is a schematic top view of an example of the medical instrument 10 shown in FIG. 1, that is, a schematic diagram of the medical instrument 10 seen from the attachment surface 30a side. In the example shown in FIG. 2, the outer peripheral edge 30c of the application member 30 (equivalent to the outer peripheral edge 32a of the second region 32) and the outer peripheral edge (equivalent to the tear portion 33) of the first region 31 are substantially rectangular with the four corners being rounded. The application member 30 has a slit 34 (i.e., a "second region slit") in the second region 32 provided from the outer peripheral edge 32a of the second region 32 toward the tear portion 33. In the example shown in FIG. 2, the slit 34 extends from the outer peripheral edge 32a to the tear portion 33, but the slit 34 may not necessarily extend to the tear portion 33.

Figure 3:
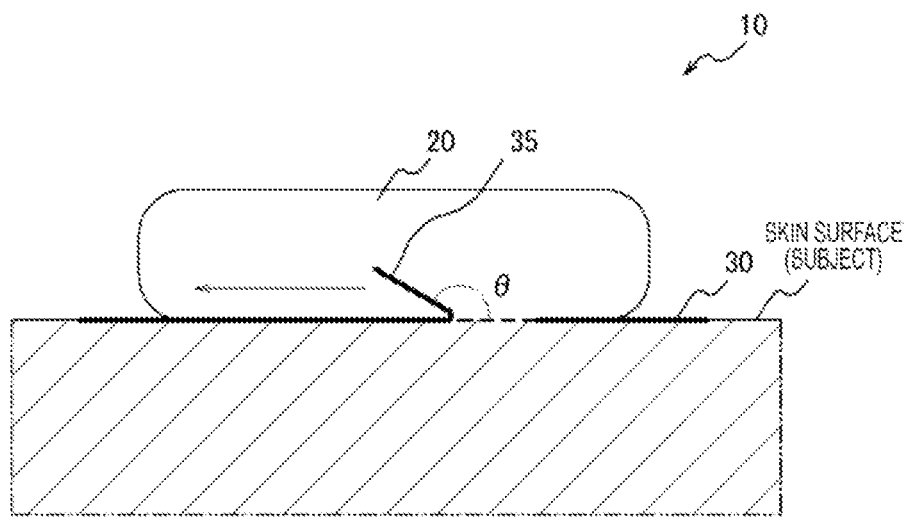
FIG. 3 is a schematic diagram exemplarily showing a second region of the medical instrument shown in FIG. 2 being peeled from the skin.

When using the medical instrument 10 shown in FIG. 2, the subject applies the application surface 30b of the application member 30 to the skin. Once the subject has finished using the medical instrument 10, the subject removes the medical instrument 10 from the skin. When removing the medical instrument 10 from the skin, the subject lifts a tongue portion 35, which is a portion of the second region 32 formed by the slit 34, with the subject's fingers and pulls the tongue portion 35 such that an angle θ between the skin and the application surface 30b of the second region 32 reaches a predetermined angle (e.g., an angle of 90 degrees or more). The subject then tears the tear portion 33 to separate the first region 31 from the second region 32 while holding down the first region 31 to which the medical device 20 is attached, for example, with the subject's hand, so that the first region 31 does not peel off the skin, and peels only the second region 32 from the skin. FIG. 3 schematically shows the second region 32 being peeled from the skin with the skin and the application surface 30b of the second region 32 forming the predetermined angle. In FIG. 3, for ease of understanding, the first region 31 that remains stuck to the skin is shown in a broken line and the second region 32 to be peeled from the skin is shown in thick solid lines.

As the second region 32 is peeled from the skin, the subject pulls the tongue portion 35 in a direction along the rectangular outer peripheral edge 32a of the second region 32 to peel the second region 32 from the skin. That is, in the example of the application member 30 shown in FIG. 2, the subject peels the second region 32 from the skin by changing the direction in which the second region 32 including the tongue portion 35 is pulled in four directions in turn.

After the second region 32 is completely peeled off the skin, the subject pulls the medical device 20 and the first region 31 to which the medical device 20 is attached upward (i.e., a direction toward the attachment surface 30a in a thickness direction) from the skin to pull them away from the skin. The subject can thus remove the entire medical instrument 10 from the skin.

The medical instrument 10 according to the present embodiment thus includes the first region 31 and the second region 32, and the adhesion of the application surface 30b is stronger in the second region 32 than in the first region 31. The medical instrument 10 does not tend to peel off the subject when the medical instrument 10 is in use due to the adhesion of the second region 32.

Additionally, the second region 32 is formed to be separable from the first region 31 by the tear portion 33. The subject can thus first peel only the second region 32 when removing the medical instrument 10. Because the medical device 20 is not attached to the second region 32, the second region 32 can be easily peeled from the skin at the predetermined angle between the skin and the application surface 30b of the second region 32. Peeling the second region 32 at the predetermined angle thus enables the second region 32 to be peeled in turn in the directions in which the second region 32 is applied from a portion of the region in which the second region 32 is applied to the skin. If the second region 32, which has strong adhesion, is peeled upward (i.e., the direction toward the attachment surface 30a in the thickness direction) from the skin, the second region 32 will be peeled in one direction so that the force on the skin increases, causing adverse events such as peeling of the epidermis. Lifting the tongue portion 35 with the subject's fingers and pulling the tongue portion 35 such that the angle θ between the skin and the application surface 30b of the second region 32 is reaches predetermined angle (e.g., an angle of 90 degrees or more) enables the force on the skin to be distributed when peeling the second region 32 to thereby prevent the epidermis from peeling off and reduce the subject's pain.

Additionally, because the first region 31 has weaker adhesive capability than the second region 32, the pain caused when removing the first region 31 and the medical device 20 from the skin is reduced compared to a case in which the entire application member 30 has strong adhesion.

Figure 4:
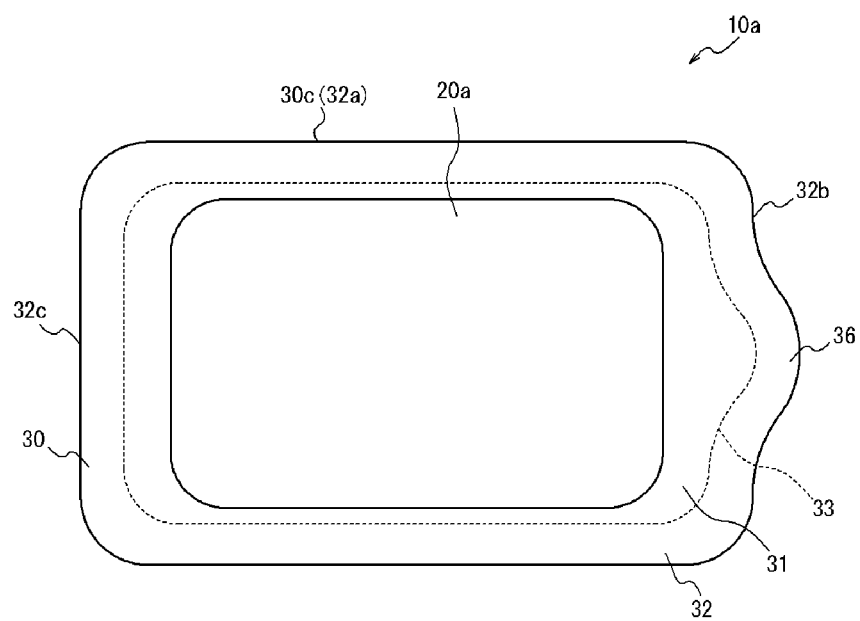
FIG. 4 is a schematic top view of another example of the medical instrument shown in FIG. 1.

FIG. 4 is a schematic top view of another example (medical instrument 10a) of the medical instrument 10 shown in FIG. 1. In the example shown in FIG. 4, similar to the example shown in FIG. 2, the outer peripheral edge 30c of the application member 30 (equivalent to the outer peripheral edge 32a of the second region 32) and the outer peripheral edge (equivalent to the tear portion 33) of the first region 31 are substantially rectangular. In the example shown in FIG. 4, the second region 32 has a protrusion 36 protruding in a direction opposite the first region 31 on one side 32b of the four sides of the outer peripheral edge 32a. The second region 32 may also have similar protrusions 36 on the other sides.

Figure 5:
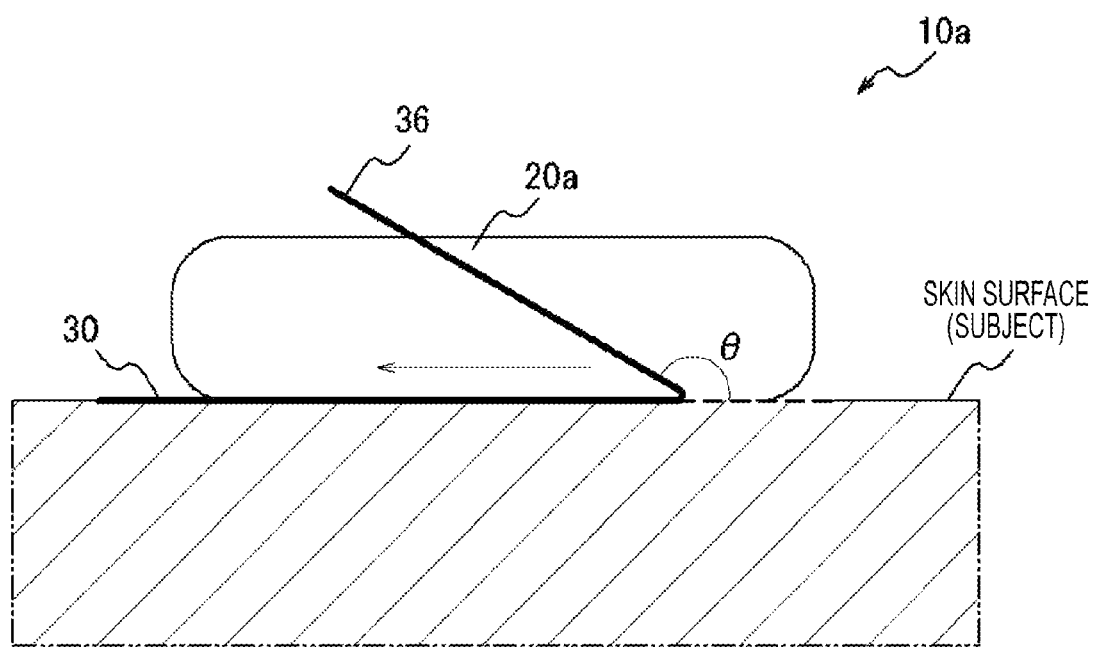
FIG. 5 is a schematic diagram exemplarily showing the second region of the medical instrument shown in FIG. 4 being peeled from the skin.

Once the subject has finished using the medical instrument 10a shown in FIG. 4, the subject removes the medical instrument 10a from the skin. When removing the medical instrument 10a from the skin, the subject lifts the protrusion 36 with the subject's fingers and pulls the protrusion 36 such that the angle θ between the skin and the application surface 30b of the second region 32 reaches the predetermined angle (e.g., an angle of 90 degrees or more). The subject then tears the tear portion 33 to separate the first region 31 and the second region 32 while holding down the first region 31 to which the medical device 20a is attached, for example, with the subject's hand so that the first region 31 does not peel off the skin, and peels only the second region 32 from the skin. FIG. 5 schematically shows the second region 32 being peeled from the skin with the skin and the application surface 30b of the second region 32 forming the predetermined angle. In FIG. 5, similarly to FIG. 3, the first region 31 that remains stuck to the skin is shown in a broken line and the second region 32 to be peeled from the skin is shown in a thick solid line.

In the example shown in FIG. 4, the subject can peel the second region 32 by pulling the protrusion 36, while holding the protrusion 36, from the side 32b on which the protrusion 36 is provided toward an opposing side 32c. In other words, in the example shown in FIG. 4, the subject can peel the second region 32 by pulling the protrusion 36 in one direction. In contrast to the example shown in FIG. 2 in which it is necessary to pull the second region 32 in four directions, in the example shown in FIG. 4, the second region 32 can be peeled from the skin by pulling the second region 32 in one direction. Thus, the second region 32 can be peeled even more easily. The manner in which to remove the first region 31 and the medical device 20a after peeling the second region 32 is the same as the example shown in FIG. 2 and description thereof is omitted.

Although in FIGS. 2 and 4, the outer peripheral edge 30c of the application member 30 and the outer peripheral edge of the first region 31 have been described as being substantially rectangular, the outer peripheral edge 30c of the application member 30 and the outer peripheral edge of the first region 31 may have shapes other than substantially rectangular. For example, the outer peripheral edge 30c of the application member 30 and the outer peripheral edge of the first region 31 may be substantially polygonal with three or five or more sides. The outer peripheral edge 30c of the application member 30 and the outer peripheral edge of the first region 31 may also be circular or oval, such as elliptical.

Figure 6:
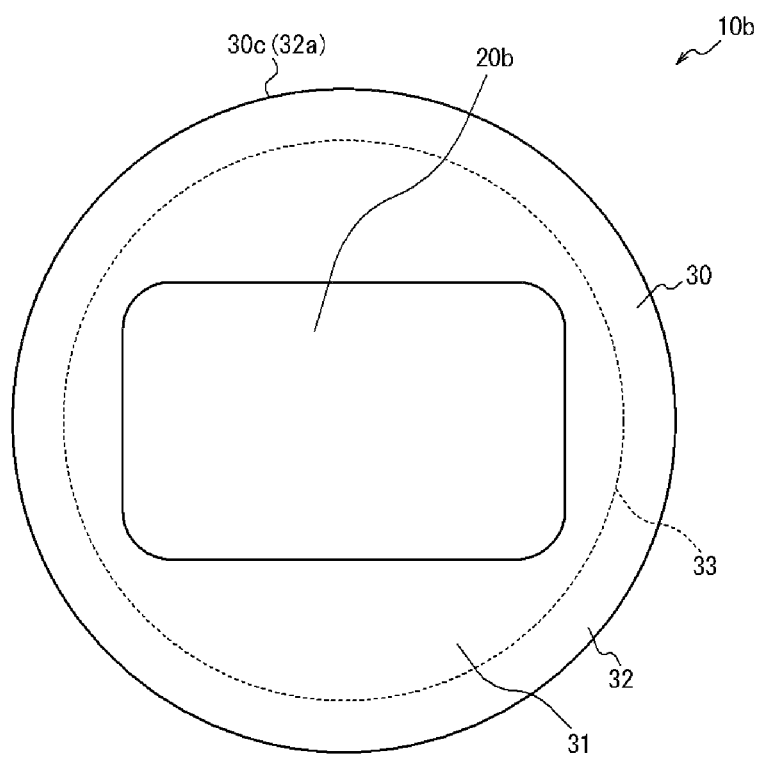
FIG. 6 is a schematic top view of still another example of the medical instrument shown in FIG. 1.

FIG. 6 is a schematic top view of still another example (medical instrument 10b) of the medical instrument 10 shown in FIG. 1 and is a schematic top view of an example in which the outer peripheral edge 30c of the application member 30 (equivalent to the outer peripheral edge 32a of the second region 32) of the medical instrument 10b is circular. As shown in FIG. 6, when the second region 32 is circular, it is easier for the subject to lift the circular outer peripheral edge 32a at any position when peeling the second region 32 from the skin. That is, in the examples shown in FIGS. 2 and 4, the position at which to lift the second region 32 (the tongue portion 35 and the protrusion 36, respectively) and the direction in which to pull the second region 32 are fixed, whereas in the example shown in FIG. 6, a portion of the second region 32 can be lifted at any position along the outer peripheral edge 32a and the second region 32 can be peeled by pulling the second region 32 from the position at which it has been lifted. After peeling the second region 32, the subject peels the first region 31 to which a medical device 20b is attached from the skin.

It has been described that the first region 31 is peeled after peeling the second region 32 when removing the medical instruments 10, 10a, and 10b. However, in the medical instruments 10, 10a, and 10b, the second region 32 may be peeled after peeling the first region 31. Configurations of the medical instrument 10, which is removed from the skin by peeling the second region 32 after peeling the first region 31, will now be described.

Figure 7:
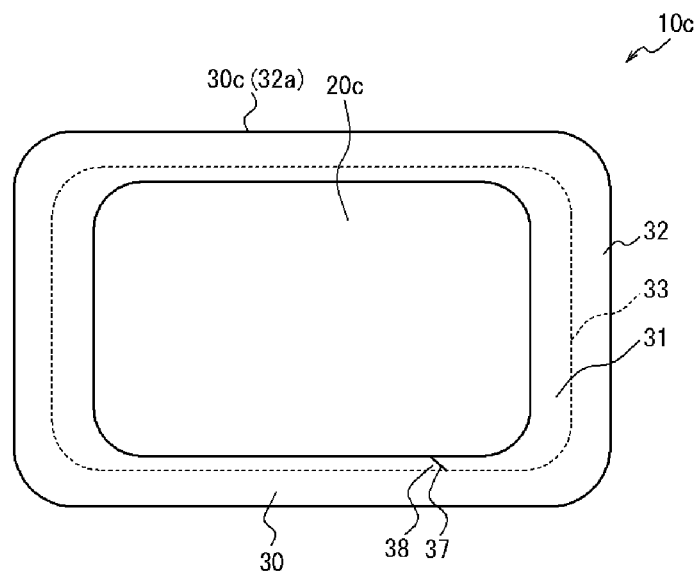
FIG. 7 is a schematic top view of still another example of the medical instrument shown in FIG. 1.

FIG. 7 is a schematic top view of still another example (medical instrument 10c) of the medical instrument 10 shown in FIG. 1. In the example shown in FIG. 7, the outer peripheral edge 30c of the application member 30 (equivalent to the outer peripheral edge 32a of the second region 32) and the outer peripheral edge (equivalent to the tear portion 33) of the first region 31 are substantially rectangular with the four corners being rounded. The application member 30 has a slit (i.e., a "first region slit") in the first region 31 provided from the tear portion 33 toward the inside (center) of the first region 31.

Once the subject has finished using the medical instrument 10c shown in FIG. 7, the subject removes the medical instrument 10c from the skin. When removing the medical instrument 10c from the skin, the subject lifts, with the subject's fingers, a tongue portion 38, which is a portion of the first region 31 formed by the slit 37 and by tearing a portion of the tear portion 33. The subject then tears the tear portion 33 completely to separate the first region 31 and the second region 32 while holding down the second region 32, for example, with the subject's hand, and pulls a medical device 20c and the first region 31 upward (i.e., the direction toward the attachment surface 30a in the thickness direction) from the skin to pull them away from the skin.

After removing the medical device 20c and the first region 31 from the skin, the subject lifts a portion of the second region 32 remaining on the skin and, in a similar manner as described with reference to FIGS. 2 and 3, pulls the tongue portion 38 such that the angle θ between the skin and the application surface 30b of the second region 32 reaches the predetermined angle (e.g., an angle of 90 degrees or more) to peel the second region 32 from the skin. The subject may, for example, sprinkle water on the second region 32 to weaken the adhesion to facilitate peeling of the second region 32 from the skin. Peeling the second region 32 in this manner enables the subject to reduce the burden on the skin when removing the entire medical instrument 10c from the skin.

Figure 8:
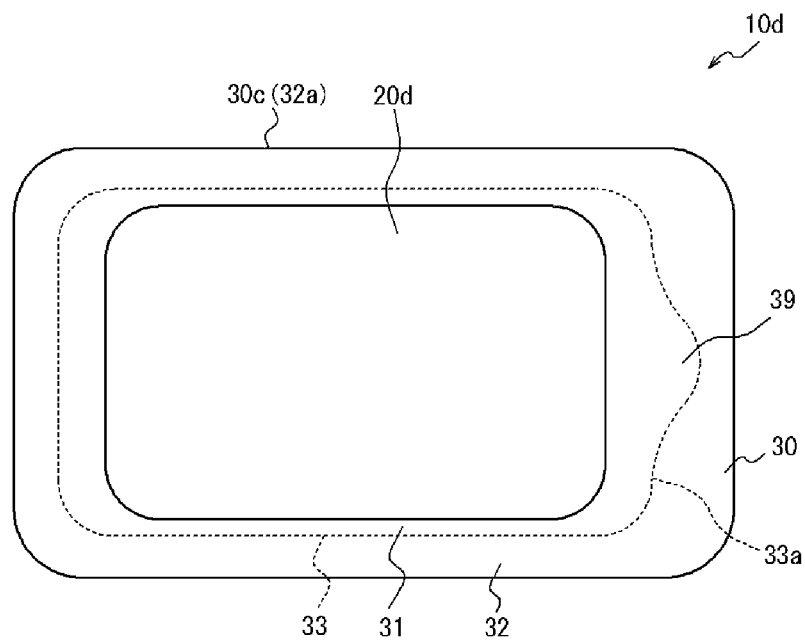
FIG. 8 is a schematic top view of still another example of the medical instrument shown in FIG. 1.

FIG. 8 is a schematic top view of still another example (medical instrument 10d) of the medical instrument 10 shown in FIG. 1. In the example shown in FIG. 8, the outer peripheral edge 30c of the application member 30 (equivalent to the outer peripheral edge 32a of the second region 32) and the outer peripheral edge (equivalent to the tear portion 33) of the first region 31 are substantially rectangular with the four corners being rounded. In the example shown in FIG. 8, the first region 31 has a protrusion 39 protruding in a direction toward the second region 32 on one side 33a of the four sides of the tear portion 33. The first region 31 may also have similar protrusions 39 on the other sides of the tear portion 33.

Once the subject has finished using the medical instrument 10d shown in FIG. 8, the subject removes the medical instrument 10d from the skin. When removing the medical instrument 10d from the skin, the subject tears the portion that forms the protrusion 39 in the tear portion 33 to separate the protrusion 39 of the first region 31 from the second region 32. The subject then lifts the protrusion 39, tears the tear portion 33 completely to separate the first region 31 and the second region 32, and removes a medical device 20d and the first region 31 from the skin.

After removing the medical device 20d and the first region 31 from the skin, the subject peels the second region 32 remaining on the skin from the skin in a similar manner as described for FIG. 7.

Although, in FIGS. 7 and 8, the outer peripheral edge 30c of the application member 30 and the outer peripheral edge of the first region 31 have been described as being substantially rectangular, the outer peripheral edge 30c of the application member 30 and the outer peripheral edge of the first region 31 may have shapes other than substantially rectangular. For example, the outer peripheral edge 30c of the application member 30 and the outer peripheral edge of the first region 31 may be substantially polygonal with three or five or more sides.

Examples have been described in which the tear portion 33 is formed on the outer peripheral edge of the first region 31, that is, between the first region 31 and the second region 32. However, the tear portion 33 may be formed inside the first region 31, for example, as shown in FIG. 9.

Figure 9:
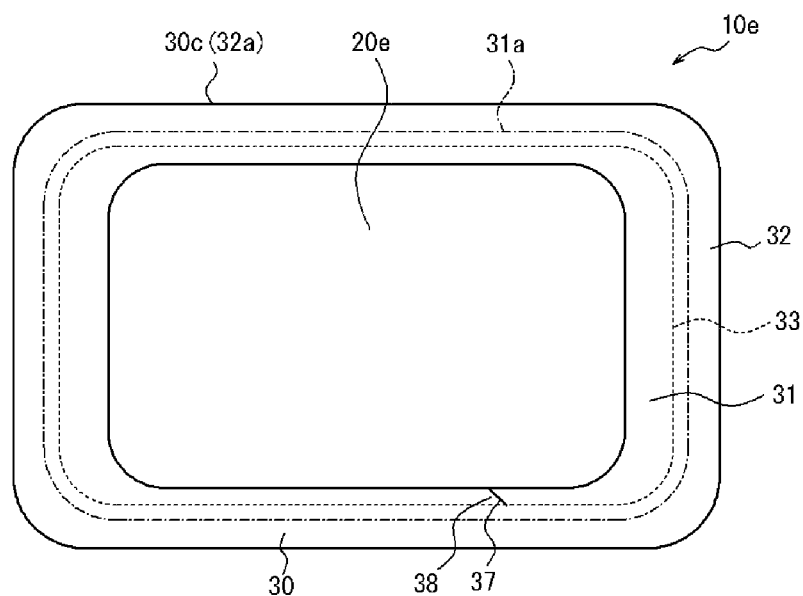
FIG. 9 is a schematic top view of still another example of the medical instrument shown in FIG. 1.

FIG. 9 is a schematic top view of still another example (medical instrument 10e) of the medical instrument 10 shown in FIG. 1. In the example shown in FIG. 9, the outer peripheral edge 30c of the application member 30 (equivalent to the outer peripheral edge 32a of the second region 32) and an outer peripheral edge 31a of the first region 31 are substantially rectangular with the four corners being rounded. The tear portion 33 is formed inside the first region 31. A medical device 20e is attached to the first region 31 inside the tear portion 33 (i.e., more toward the center of the first region 31 than the tear portion 33). The application member 30 has the slit 37 in the first region 31 provided from the tear portion 33 toward the center of the first region 31.

Once the subject has finished using the medical instrument 10e shown in FIG. 9, the subject removes the medical instrument 10e from the skin. When removing the medical instrument 10e from the skin, the subject lifts, with the subject's fingers, the tongue portion 38, which is a portion of the first region 31 formed by the slit 37 and by tearing a portion of the tear portion 33. The subject then tears the tear portion 33 completely to separate a region surrounded by the tear portion 33, the region being a first portion of the first region 31, and pulls the medical device 20e and the portion of the first region 31 surrounded by the tear portion 33 upward (i.e., the direction toward the attachment surface 30a (see, FIG. 1) in the thickness direction) from the skin to pull them away from the skin.

After removing the medical device 20e and the first portion of the first region 31 from the skin, the subject peels the portion of the first region 31 remaining on the skin and the second region 32 from the skin. The manner in which the subject peels the portion of the first region 31 remaining on the skin and the second region 32 from the skin is, for example, similar to the manner as described with reference to FIG. 7 above. The subject can thus reduce the burden on the skin when removing the entire medical instrument 10e from the skin.

In FIG. 2, it has been described that the second region 32 has one slit 34. However, the second region 32 may have two slits as shown, for example, in FIGS. 10 and 11.

Figure 10:
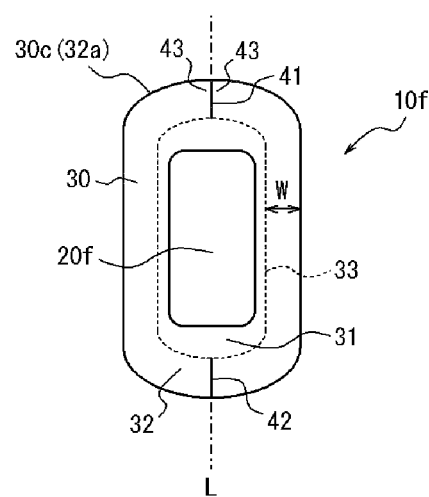
FIG. 10 is a schematic top view of still another example of the medical instrument shown in FIG. 1.
Figure 11:
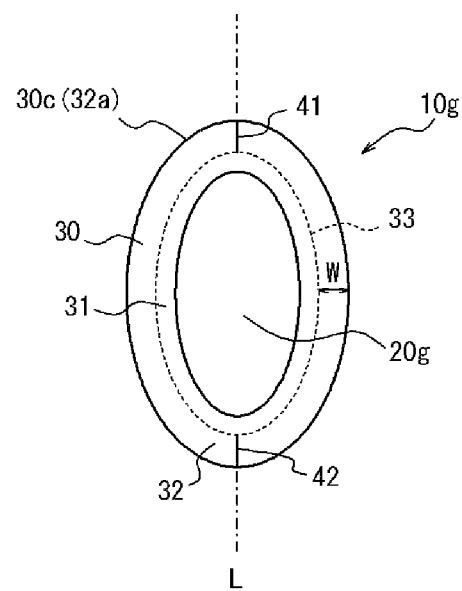
FIG. 11 is a schematic top view of still another example of the medical instrument shown in FIG. 1.

FIGS. 10 and 11 are schematic top views of still other examples (medical instrument 10f and medical instrument 10g) of the medical instrument 10 shown in FIG. 1. In each of the examples shown in FIGS. 10 and 11, the outer peripheral edge 30c of the application member 30 (equivalent to the outer peripheral edge 32a of the second region 32) and the outer peripheral edge (equivalent to the tear portion 33) of the first region 31 are oval. Oval here includes, for example, elliptical, oblong, egg-shaped, and race track-shaped (oblong with rounded corners). FIG. 10 shows the example in which the outer peripheral edge 30c of the application member 30 and the outer peripheral edge of the first region 31 are race track-shaped, and FIG. 11 shows the example in which the outer peripheral edge 30c of the application member 30 and the outer peripheral edge of the first region 31 are elliptical.

In each of the examples shown in FIGS. 10 and 11, the second region 32 has two slits 41 and 42 (i.e., "second region slits") that connect the outer peripheral edge 32a of the second region 32 with the tear portion 33. The second region 32 is separated into two parts when it is peeled from the skin by the two slits 41 and 42 and the tear portion 33. In each of the examples shown in FIGS. 10 and 11, the two slits 41 and 42 extend linearly substantially in parallel. More specifically, in each of the examples shown in FIGS. 10 and 11, the two slits 41 and 42 extend linearly along a longitudinal axis of the oval shape of the application member 30. Furthermore, in each of the examples shown in FIGS. 10 and 11, the two slits 41 and 42 are arranged on a straight line L. In each of the examples shown in FIGS. 10 and 11, the straight line L is the longitudinal axis of the oval. The longitudinal axis is, for example, a longitudinal axis of symmetry of the line-symmetric oval.

In each of the examples shown in FIGS. 10 and 11, the tear portion 33 does not have a portion that extends in a direction perpendicular to the direction of extension of the slits 41 and 42. That is, in each of these examples, the tear portion 33 does not have a portion that extends in a direction perpendicular to the straight line L.

Once the subject has finished using the medical instrument 10f shown in FIG. 10, the subject removes the medical instrument 10f from the skin. When removing the medical instrument 10f from the skin, the subject first separates the second region 32 into two parts by the two slits 41 and 42 and the tear portion 33 that has been torn and peels the second region 32 from the skin in two actions. When peeling the second region 32 from the skin by separating the second region 32 into two parts, the subject can peel the second region 32 separated into two parts without passing a portion (e.g., the protrusion 36) of the second region 32 that has been peeled over the medical device 20a as, for example, in the case of peeling the second region 32 of the medical instrument 10a shown in FIG. 4. Thus, the medical instrument 10f shown in FIG. 10 enables the subject to peel the second region 32 separated into two parts one by one with one hand while holding a medical device 20f with the other hand. This can improve the manipulability when peeling (removing) the second region 32 from the skin.

Additionally, when peeling the second region 32, the subject peels the second region 32 separated into two parts from the side of one of the slits toward the side of the other slit. As one example, an example will be described in which the second region 32 is peeled from the side of the slit 41 toward the side of the slit 42. The subject lifts a tongue portion 43 formed by the slit 41 to peel one of the two parts into which the second region 32 is separated from the side of the slit 41 toward the side of the slit 42. The subject can then peel the second region 32 along the straight line L. After peeling one of the two parts into which the second region 32 is separated, the subject peels the other part of the second region 32 in a similar manner. That is, the subject peels the other part of the second region 32 along the straight line L from the side of the slit 41 toward the side of the slit 42. The subject can thus peel the second region 32 separated into two parts in one direction (from the slit 41 side toward the slit 42 side) along the straight line L. Enabling the second region 32 to be peeled in one direction can reduce the pain caused when peeling the second region 32, for example, by enabling the second region 32 to be peeled in a direction along the body hair. Additionally, because the tear portion 33 does not have a portion that extends in the direction perpendicular to the direction of extension of the slits 41 and 42, the subject can easily peel the second region 32 separated into two parts along the direction of extension of the slits 41 and 42 (the straight line L).

After peeling the second region 32, the subject can remove the first region 31 and the medical device 20f in a similar manner as the example shown in FIG. 2.

In the example shown in FIG. 11, the subject can also peel the second region 32 separated into two parts in one direction along the straight line L, similar to the example shown in FIG. 10. Thus, if the second region 32 is peeled in the direction along the body hair, the pain caused when peeling the second region 32 can be reduced.

In each of the examples shown in FIGS. 10 and 11, the application member 30 is oval. If the application member 30 is square such as rectangular, the adhesive applied to the application surface 30b (see, FIG. 1) will tend to remain on the subject's skin at the location of the four corners of the second region 32 when peeling the second region 32 from the skin. However, in the case in which the application member 30 is oval as shown in FIGS. 10 and 11, the second region 32 does not have any corners so that the adhesive does not tend to remain on the subject's skin.

In each of the examples shown in FIGS. 10 and 11, a width W of the second region 32 is preferably uniform. If the width W of the second region 32 is not uniform, the force on the second region 32 when the subject peels the second region 32 will be concentrated or distributed according to changes in the width W of the second region 32. In contrast, in the case in which the width W of the second region 32 is uniform, the force on the second region 32 will not tend to be concentrated or distributed, and thus the second region 32 is prevented from peeling in a way not intended by the subject.

Examples in which the application member 30 is formed as a one-piece member has been described but the application member may be composed of two members. An example of the medical instrument including the application member 30 that is composed of two members will now be described.

Figure 12:
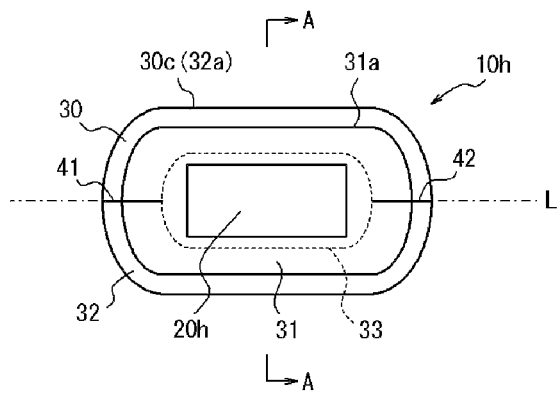
FIG. 12 is a schematic top view of an example of the medical instrument having an application member composed of two members.

FIG. 12 is a schematic top view of an example (medical instrument 10h) of the medical instrument with an application member 30 that is composed of two members. In the example shown in FIG. 12, the outer peripheral edge 30c of the application member 30 (equivalent to the outer peripheral edge 32a of the second region 32) and the outer peripheral edge 31a of the first region 31 are race track-shaped oval in shape. In the example shown in FIG. 12, the tear portion 33 is formed inside the first region 31. A medical device 20h is attached to the first region 31 inside the tear portion 33 (i.e., more toward the center of the first region 31 than the tear portion 33). The application member 30 has, in the first region 31 and the second region 32, the two slits 41 and 42 that connect the outer peripheral edge 32a of the second region 32 with the tear portion 33. The slits 41 and 42 are arranged on the straight line L that indicates the longitudinal axis of the oval. The application member 30 is composed of a first member 51 and a second member 52.

Figure 13:
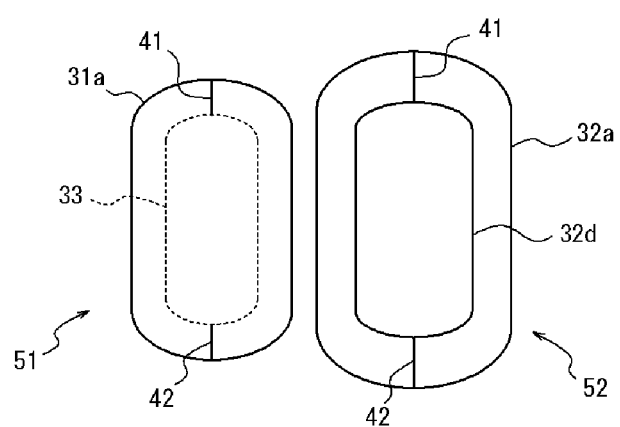
FIG. 13 is a schematic top view of a first member and a second member that compose the application member.

FIG. 13 is a schematic top view of the first member 51 and the second member 52 that compose the application member 30. The first member 51 is a sheet-like member having an application surface that is applied to the subject's skin, and is made, for example, of a sheet-like polyurethane, polyethylene, or other dressing material. An adhesive is applied to the application surface of the first member 51. The first member 51 has the tear portion 33 and the two slits 41 and 42.

The second member 52 is a sheet-like member having an application surface that is applied to the subject's skin, and is made, for example, of a nonwoven tape. The second member 52 is formed annularly having the outer peripheral edge 32a and an inner peripheral edge 32d. In the example shown in FIG. 12, the outer peripheral edge 32a and the inner peripheral edge 32d are race track-shaped oval, but the shapes of the outer peripheral edge 32a and the inner peripheral edge 32d are not limited to oval. An adhesive is applied to the application surface of the second member 52. The adhesive is applied to the second member 52 by selecting the material of the adhesive, the method of applying the adhesive, or the like, as appropriate such that the adhesion of the application surface of the second member 52 is stronger than the adhesion of the application surface of the first member 51.

The first member 51 and the second member 52 are laid on top of each other to form the application member 30. In the application member 30, the second member 52 may be laid on the application surface of the first member 51 or the first member 51 may be laid on the application surface of the second member 52. FIG. 12 shows an example of the second member 52 laid on the application surface of the first member 51. The first member 51 and the second member 52 are fixed together by the adhesion of the adhesive applied to the application surfaces to form the application member 30.

The inner peripheral edge 32d of the second member 52 is positioned outside the tear portion 33 of the first member. The outer peripheral edge 31a of the first member 51 is positioned outside the inner peripheral edge 32d of the second member 52. When the application member 30 in which the first member 51 and the second member 52 are laid on top of each other is viewed from the top, the tear portion 33 lies within the inner peripheral edge 32d. Thus, tearing the tear portion 33 when removing the application member 30 from the skin enables the entire second member 52 having stronger adhesion to be separated from a portion of the first member 51 defined by the tear portion 33.

Additionally, the outer peripheral edge 32a of the second member 52 is positioned outside the outer peripheral edge 31a of the first member 51. When the application member 30 in which the first member 51 and the second member 52 are laid on top of each other is viewed from the top, the outer peripheral edge 31a lies within the outer peripheral edge 32a. Thus, the outer peripheral edge 30c of the application member 30 is formed, throughout its entire perimeter, by the second member 52 having strong adhesion. This helps to prevent the application member 30 from inadvertently peeling off the skin.

Figure 14:
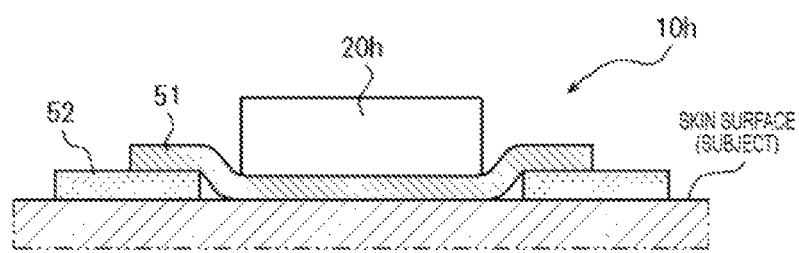
FIG. 14 is a schematic cross-sectional view of the medical instrument shown in FIG. 12 in use.

FIG. 14 is a schematic cross-sectional view of the medical instrument 10h shown in FIG. 12 in use. That is, FIG. 14 shows the medical instrument 10h attached to the subject's skin. FIG. 14 shows, in particular, a cross section taken along line A-A in FIG. 12. As shown in FIG. 14, when the medical instrument 10h is in use, the application surface of the second member 52 is attached to the subject's skin at both ends of the application member 30 in the cross section A-A, and the application surface of the first member 51 is attached to the subject's skin at the center of the application member 30 in the cross section A-A.

When removing the medical instrument 10h, the subject first tears the tear portion 33 and peels the outer peripheral portion of the tear portion 33 formed by a portion of the first member 51 and the second member 52. At this time, the subject can remove a portion of the application member 30 along the straight line L, for example, in a similar manner as described in the example shown in FIG. 10. The subject then peels the portion surrounded by the tear portion 33 formed by a portion of the first member 51. The application member 30 can thus be composed of two members. Composing the application member 30 with two members enables the force on the skin to be distributed when peeling the portion having strong adhesion to thereby prevent the epidermis from peeling off and reduce the subject's pain.

While the present invention has been described with reference to various drawings and embodiments, it should be noted that many variations and modifications can easily be made by those skilled in the art based on the present disclosure. It is thus noted that such variations and modifications are included in the scope of the present invention.

Figure 15:
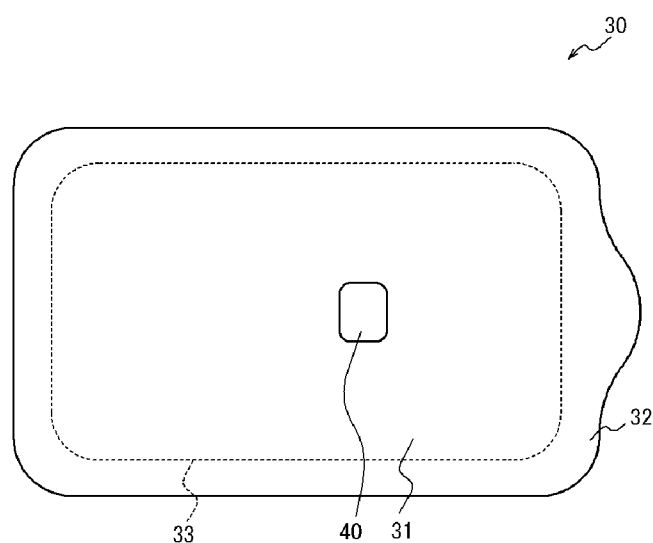
FIG. 15 is a schematic diagram of a variation of an application member shown in FIG. 1.

For example, the application member 30 may further have a third region 40 in a portion of the first region 31, as shown in FIG. 15. The adhesion of the application surface 30b is stronger in the third region 40 than in the first region 31 surrounding the third region 40. Providing the third region 40 having stronger adhesion than the surrounding first region 31 in a portion of the first region 31 thus enables the application member 30 to be adhered to the skin more strongly at the portion in which the third region 40 is provided in the first region 31 having weaker adhesion than the second region 32.

The third region 40 such as this is particularly effective, for example, when there is a first portion that preferably does not come off the skin in the medical device 20 attached to the attachment surface 30a of the first region 31. That is, providing the third region 40 at a position to which the first portion is attached on the attachment surface 30a helps to ensure adhesion between the first portion and the skin. For example, in a case in which the medical device 20 has a sensor for detecting biological information, the third region 40 is preferably provided at a position to which the sensor is attached on the attachment surface 30a such that the position of the sensor is fixed relative to the skin.

Additionally, although in the embodiments described above, the outer peripheral edge 32a and the tear portion 33 of the application member 30 have substantially similar shapes, the outer peripheral edge 32a and the tear portion 33 may have different shapes. For example, the outer peripheral edge 32a may be circular and the tear portion may be substantially rectangular.

Additionally, with a view to reducing the subject's pain, the area of the second region 32 is preferably as small as possible. The smaller the area of the second region 32 having strong adhesion, the less the pain felt by the subject when the second region 32 is peeled.

Figure 16:
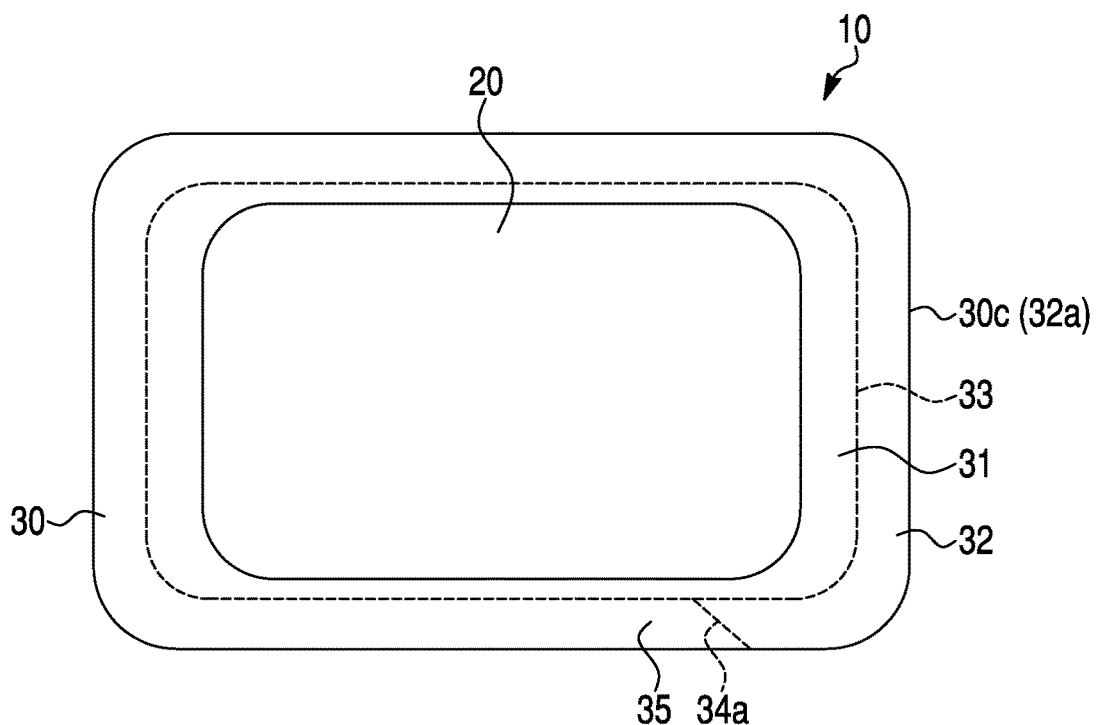
FIG. 16 is a schematic top view of an example of the medical instrument shown in FIG. 2, except including a second region tear portion instead of a second region slit.
Figure 17:
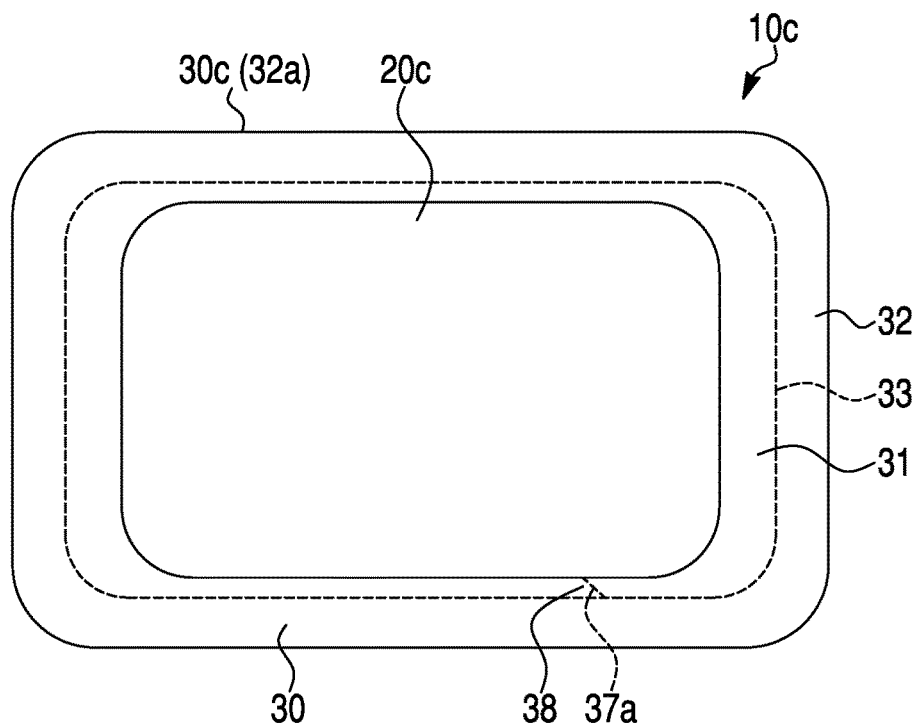
FIG. 17 is a schematic top view of an example of the medical instrument shown in FIG. 7, except including a first region tear portion instead of a first region slit.
Figure 18:
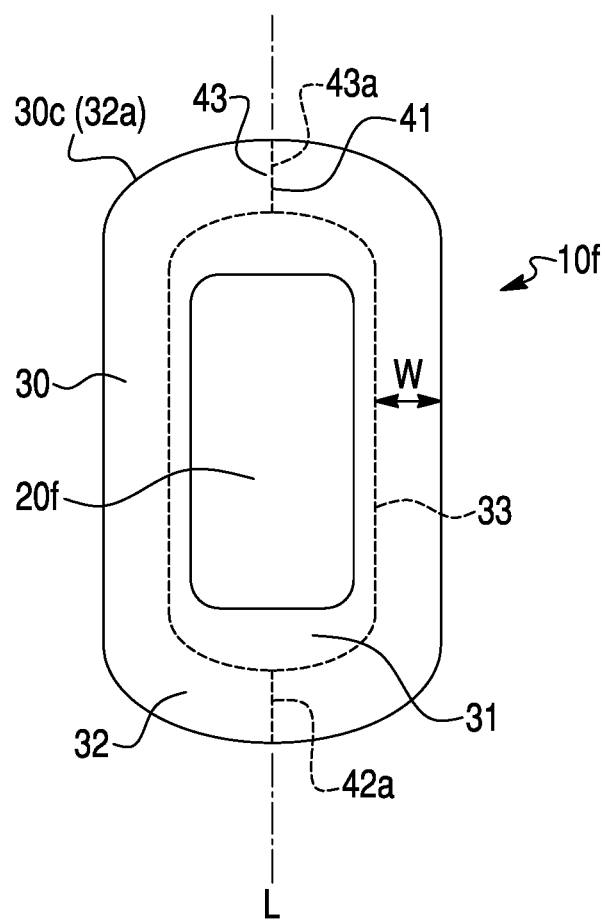
FIG. 18 is a schematic top view of an example of the medical instrument shown in FIG. 10, except including second region tear portions instead of second region slits.

Furthermore, although it has been described that in the medical instruments 10, 10c, and 10e to 10h shown in FIGS. 2, 7, and 9 to 14, the second region 32 and the first region 31 have slits 34, 37, 41, and 42, the second region 32 and the first region 31 may have a tear portion 34a, 47a, 41a, 42a such as a perforation in place of the slits 34, 37, 41, and 42. FIG. 16 is a schematic top view of an example of the medical instrument shown in FIG. 2, except including a second region tear portion 34a instead of a second region slit 34. FIG. 17 is a schematic top view of an example of the medical instrument shown in FIG. 7, except including a first region tear portion 37a instead of a first region slit 37. FIG. 18 is a schematic top view of an example of the medical instrument shown in FIG. 10, except including second region tear portions 42a, 43a instead of second region slits 42, 43. If the second region 32 and the first region 31 have a tear portion 34a, 37a, 41a, 42a in place of the slits 34, 37, 41, and 42, the subject can form the slits 34, 37, 41, and 42 in the second region 32 and the first region 31 by tearing the tear portion 34a, 37a, 41a, 42a.

REFERENCE NUMERAL LIST 10, 10a, 10b, 10c, 10d, 10e, 10f, 10g, 10h Medical instrument
20, 20a, 20b, 20c, 20d, 20e, 20f, 20g, 20h Medical device
30 Application member
30a Attachment surface
30b Application surface
30c, 31a, 32a Outer peripheral edge
31 First region
32 Second region
32b, 32c, 33a Side
32d Inner peripheral edge
33 Tear portion
34, 37, 41, 42 Slit
35, 38, 43 Tongue portion
36, 39 Protrusion
40 Third region
51 First member
52 Second member
L Longitudinal axis of the oval shape
W Width of the second region

What is claimed is:

1. A sheet-shaped application member comprising:
a first region, a second region extending around the first region, and a third region in a portion of the first region, wherein:
the first region comprises a first region attachment surface to which a medical device is attachable, and a first region application surface opposite the first region attachment surface and adapted to be applied to a subject,
the second region comprises a second region application surface adapted to be applied to the subject,
the third region comprises a third region application surface adapted to be applied to the subject,
the first region application surface and the second region application surface are adapted such that, when the application member is applied to the subject, adhesion at the second region application surface is stronger than adhesion at the first region application surface, and
the third region is adapted such that, when the application member is applied to the subject, adhesion at the third region application surface is stronger than adhesion at an area surrounding the third region application surface; and
an application member tear portion adapted to allow for tearing of a portion within the first region or for tearing the first region from the second region.

2. The application member according to claim 1, wherein the first region comprises a first region slit or a first region tear portion extending from the application member tear portion toward a center of the first region.

3. The application member according to claim 1, wherein the second region comprises a second region slit or a second region tear portion extending from an outer peripheral edge of the second region toward the application member tear portion.

4. The application member according to claim 1, wherein an outer peripheral edge of the second region is substantially polygonal, and the second region comprises a protrusion protruding in a direction opposite the first region on at least one side of the second region.

5. The application member according to any claim 1, wherein the first region is substantially polygonal and comprises a protrusion protruding toward the second region on at least one side of the first region.

6. The application member according to claim 1, wherein the second region is oval-shaped.

7. The application member according to claim 1, wherein the second region comprises at least two second region slits or at least two second region tear portions connecting an outer peripheral edge of the second region with the application member tear portion.

8. The application member according to claim 7, wherein the at least two second region slits or the at least two second region tear portions extend linearly substantially in parallel.

9. The application member according to claim 8, wherein the application member is oval and the at least two second region slits or the at least two second region tear portions extend linearly substantially in parallel along a longitudinal axis of the oval.

10. A medical instrument comprising:
a medical device; and
a sheet-shaped application member comprising:
   a first region, a second region extending around the first region, and a third region in a portion of the first region, wherein:
      the first region comprises a first region attachment surface to which the medical device is attached, and a first region application surface opposite the first region attachment surface and adapted to be applied to a subject,
      the second region comprises a second region application surface adapted to be applied to the subject,
      the third region comprises a third region application surface adapted to be applied to the subject,
      the first region application surface and the second region application surface are adapted such that, when the application member is applied to the subject, adhesion at the second region application surface is stronger than adhesion at the first region application surface, and
      the third region is adapted such that, when the application member is applied to the subject, adhesion at the third region application surface is stronger than adhesion at an area surrounding the third region application surface, and
   an application member tear portion adapted to allow for tearing of a portion within the first region or for tearing the first region from the second region.

11. A sheet-shaped application member comprising:
a first region, and a second region extending around the first region, wherein:
   the first region comprises a first region attachment surface to which a medical device is attachable, and a first region application surface opposite the first region attachment surface and adapted to be applied to a subject,
   the second region comprises a second region application surface adapted to be applied to the subject, and
   the first region application surface and the second region application surface are adapted such that, when the application member is applied to the subject, adhesion at the second region application surface is stronger than adhesion at the first region application surface; and
an application member tear portion adapted to allow for tearing of a portion within the first region or for tearing the first region from the second region,
wherein the first region is substantially polygonal and comprises a protrusion protruding toward the second region on at least one side of the first region.

* * * * *